(12) United States Patent
Shiu et al.

(10) Patent No.: US 7,807,626 B2
(45) Date of Patent: Oct. 5, 2010

(54) TUMOR SUPPRESSOR PROTEIN AND NUCLEOTIDE ENCODING SAME

(75) Inventors: Stephen Yuen Wing Shiu, Hong Kong (HK); Kwok Ming Yao, Hong Kong (HK)

(73) Assignee: The University of Hong Kong, Hong Kong (CN)

(*) Notice: Subject to any disclaimer, the term of this patent is extended or adjusted under 35 U.S.C. 154(b) by 368 days.

(21) Appl. No.: 11/761,724

(22) Filed: Jun. 12, 2007

(65) Prior Publication Data

US 2009/0062189 A1    Mar. 5, 2009

Related U.S. Application Data

(60) Provisional application No. 60/814,315, filed on Jun. 16, 2006.

(51) Int. Cl.
*A61K 38/00* (2006.01)
(52) U.S. Cl. ........................................ 514/2; 424/184.1
(58) Field of Classification Search ..................... 514/2; 424/184.1
See application file for complete search history.

(56) References Cited

U.S. PATENT DOCUMENTS

2004/0043926 A1* 3/2004 Gerlach et al. ................. 514/12

OTHER PUBLICATIONS

Mellman I, 2006, The Scientist, 20(1): 47-56.*
Kaiser (Science, 2006, 313, 1370).*
Bodey et al, 2000, Anticancer Res, 20: 2665-2676.*

* cited by examiner

*Primary Examiner*—Larry R. Helms
*Assistant Examiner*—Minh-Tam Davis
(74) *Attorney, Agent, or Firm*—Robert D. Katz; Cooper & Dunham LLP

(57) ABSTRACT

The invention provides a method for suppressing tumor cell growth in a patient, comprising: administering to the patient an effective amount of an expression vector including a polynucleotide encoding a tumor suppressor protein having SEQ ID NO: 1 under conditions wherein the expression vector incorporates itself into the tumor cell genome and inhibits cell proliferation or induces cell death.

The invention further provides a method for a method for inhibiting tumor cell proliferation in a tumor cell population comprising: administering to the tumor cell population an amount of a composition comprising a tumor suppressor protein having SEQ ID NO: 1 effective to inhibit tumor cell proliferation therein.

4 Claims, 11 Drawing Sheets

TUMOR SUPPRESSOR PROTEIN AND NUCLEOTIDE ENCODING SAME

CROSS REFERENCE TO RELATED APPLICATION

This application claims the benefit of U.S. Provisional Patent Application No. 60/814,315, filed Jun. 16, 2006, the entire contents of which are incorporated herein by reference.

FIELD OF THE INVENTION

The present invention relates to a tumor suppressor protein useful as an anti-cancer agent, to nucleotides that encode for such tumor suppressor protein, and the expression vectors including the foregoing nucleotide.

BACKGROUND OF THE INVENTION

In 2002, it was estimated that there were 10.9 million new cases of cancer and 6.7 million cancer-related deaths worldwide. Globally, prostate cancer has become the third most common cancer in men, with half a million new cases each year, amounting to about 10% of all male cancers. It is the most common cancer after skin cancer, and is the second leading cause of cancer-related death in men in the United States. Breast cancer is the most frequent cancer of women, accounting for 23% of all cancers. Liver cancer is the fifth most common cancer in the world, and most of the liver cancer cases occur in developing countries, especially the Far East and Southeast Asia. The prevalence of liver cancer in developing countries and the emergence of prostate cancer and breast cancer as public health problems in developed countries have put tremendous pressure on the healthcare systems to provide new and effective treatments.

Current understanding of cancer cell biology has allowed scientists to develop a rational approach to combat cancer cells by using a combination of anti-cancer drugs, which would inactivate and/or activate, respectively, multiple targets in cell growth-promoting and growth-inhibitory signaling pathways. Clearly, there is an unmet clinical need to develop novel therapeutic agents which can act effectively alone and/or in combination with conventional radiation or chemotherapy to halt or reverse the progression of advanced cancer. Such demand has fueled the search for novel endo-/para-/autocrine growth-promoting and growth-inhibitory signaling pathways important in cancer pathogenesis, which may yield new therapeutic agents or targets for anti-cancer drug discovery and development.

PDZ domain-containing protein 2 (PDZD2) (also named KIAA0300, PIN-1, PAPIN, activated in prostate cancer (AIPC), and PDZ domain-containing protein 3 (PDZK3)), is a six-PDZ (for PSD95, Discs-large, and ZO-1) domain protein which is expressed in multiple tissues. Though proteins containing PDZ domains have been shown to bind specific C-terminal protein sequences of transmembrane receptors or ion channels, and are believed to be involved in mediating intracellular protein-protein interactions, protein scaffolding and intracellular signaling, the functions of PDZD2 in humans are as yet little understood.

SUMMARY OF THE INVENTION

The present invention relates to sPDZD2, a cleavage product of PDZD2, and a method for inhibiting or retarding cancer growth comprising administering an effective cancer growth inhibiting or retarding amount of this compound to a patient.

Accordingly, the present invention provides a tumor suppressor protein, a polynucleotide encoding the protein, an expression vector containing the polynucleotide and a cell transformed with the expression vector. The present invention also provides a method for suppressing proliferation of cancer cells. The present invention further provides a pharmaceutical composition for preventing or treating cancer comprising the polynucleotide in a pharmaceutically acceptable carrier. In accordance with one aspect of the present invention, the invention provides a tumor suppressor protein isolated from humans which has the amino acid sequence of SEQ ID NO: 1.

The present invention also provides growth-inhibitory functions for human sPDZD2 protein on prostate, breast and liver cancers. The present invention further provides for a method of inhibiting the growth of a prostate cancer cell line in a mammal comprising administering to the mammal of recombinant human sPDZD2 to inhibit the cancer growth.

DETAILED DESCRIPTION OF THE PREFERRED EMBODIMENTS

Figure 1A:
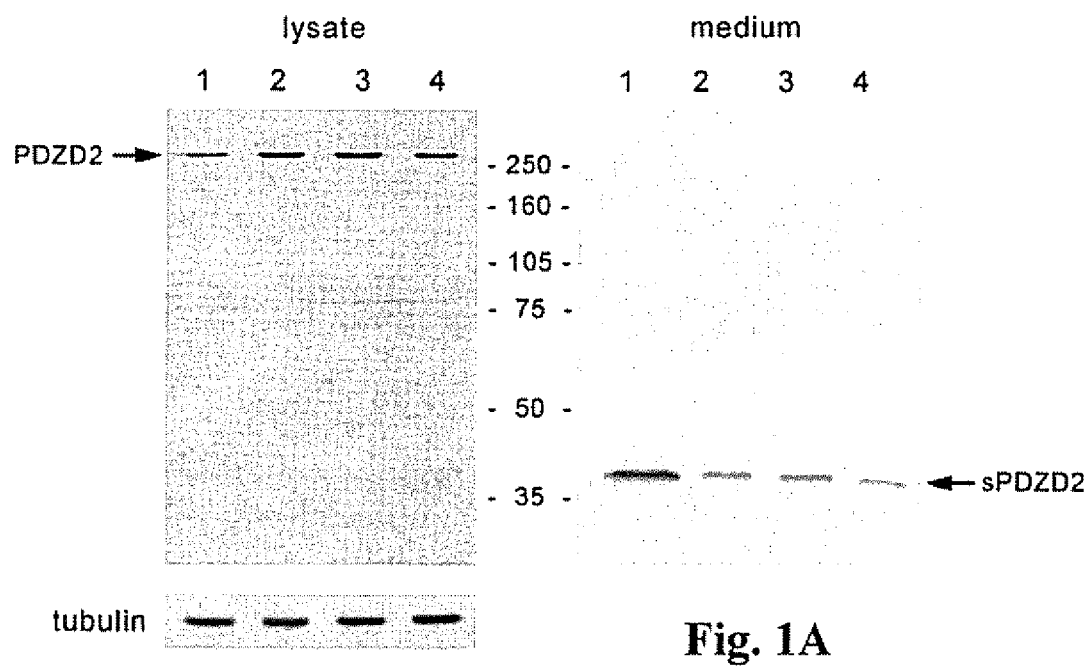
FIG. 1A shows the expression and secretion of PDZD2/sPDZD2 in prostate cancer cells. The presence of PDZD2 and sPDZD2 in cell lysates and concentrated conditioned media of (Lane 1) LNCaP, (Lane 2) DU145, (Lane 3) PC-3, and (Lane 4) 22Rv1 cells were detected by immunoblotting, using rabbit anti-PDZD2 antiserum (1:10,000 dilution).

The present invention identified the growth-inhibitory and retarding functions for human sPDZD2 protein on cancers, particularly prostate, breast and liver cancers. The present invention also provides for a method of inhibiting the growth of a prostate cancer cell line in a mammal comprising administering to the mammal of recombinant human sPDZD2 to inhibit the cancer growth.

EXAMPLE 1

Amino Acid Sequences of Human PDZD2 and sPDZD2 Protein

The primary and secondary accession numbers for the protein sequence of human PDZD2 protein as deposited in the Swiss-Prot database are, respectively, O15018 and Q9BXD4.

The tumor suppressor protein of the present invention, i.e., human sPDZD2 protein has the amino acid sequence of SEQ ID NO: 1 (one letter amino acid code) which is listed below:

```
                                             SEQ ID NO: 1
LDKLCSEDYSAGPSAVLFKTELEITPRRSPGPPAGGVSCPEKGGNRACPG

GSGPKTSAAETPSSASDTGEAAQDLPFRRSWSVNLDQLLVSAGDQQRLQS
```

```
                                                -continued
VLSSVGSKSTILTLIQEAKAQSENEEDVCFIVLNRKEGSGLGFSVAGGTD

VEPKSITVHRVFSQGAASQEGTMNRGDFLLSVNGASLAGLAHGNVLKVLH

QAQLHKDALVVIKKGMDQPRPSARQEPPTANGKGLLSRKTIPLEPGIGRS

VAVHDALCVEVLKTSAGLGLSLDGGKSSVTGDGPLVIKRVYKGGAAEQAG

IIEAGDEILAINGKPLVGLMHFDAWNIMKSVPEGPVQLLIRKHRNSS
```

Various substitution, addition and/or deletion of the amino acid residues of the protein may be performed without adversely affecting the protein's function. Further, a portion of the protein may be used when a specific purpose is to be fulfilled. The term "the tumor suppressor protein of the present invention" used herein includes these modified amino acids and fragments thereof. Therefore, the present invention includes, in its scope, a polypeptide having substantially the same amino acid sequence as the sPDZD2 protein having the amino acid sequence of SEQ ID NO: 1 and a fragment thereof. As used herein, "substantially the same polypeptide" refers to a polypeptide whose amino acid sequence shows preferably 80% or more, more preferably 90% or more, most preferably 95% or more homology to the amino acid sequence of SEQ ID NO: 1.

The sPDZD2 protein of the present invention may be encoded by a polynucleotide comprising a nucleotide sequence deduced from the amino acid sequence of the sPDZD2 protein according to the genetic code (hereinafter called "sPDZD2 gene"). It is known that several different codons encoding a same amino acid may exist due to the codon degeneracy, and, therefore, the sPDZD2 gene of the present invention may include various nucleotide sequences deduced from the amino acid sequence of the sPDZD2 protein. A preferred sPDZD2 gene has the nucleotide sequence of SEQ ID NO: 2.

```
                                                                  SEQ ID NO: 2
cttgacaagc tctgcagcga ggattactca gcagggccga gcgccgtgct cttcaaaact gagctggaga tcaccccag gaggtcacct ggccctcctg ctggaggcgt ttcgtgtccc gagaagggcg ggaacagggc ctgtccagga ggaagtggcc ctaaaaccag tgctgctgag acacccagtt cagccagtga tacgggtgaa gctgcccagg atctgccttt tagaagaagc tggtcagtta atttggatca acttctagtc tcagcggggg accagcaaag attacagtct gttttatcgt cagtgggatc gaaatctacc atcctaactc tcattcagga agcgaaagca caatcagaga atgaagaaga tgtttgcttc atagtcttga atagaaaaga aggctcaggt ctgggattca gtgtggcagg agggacagat gtggagccaa aatcaatcac ggtccacagg gtgttttctc aggggcggc ttctcaggaa gggactatga accgagggga tttccttctg tcagtcaacg gcgcctcact ggctggctta gcccacggga atgtcctgaa ggttctgcac caggcacagc tgcacaaaga tgccctcgtg gtcatcaaga aagggatgga tcagcccagg ccctctgccc ggcaggagcc tcccacagcc aatgggaagg gtttgctgtc cagaaagacc atcccctgg agcctggcat tgggagaagt gtggctgtac acgatgctct gtgtgttgaa gtgctgaaga cctcggctgg gctgggactg agtctggatg ggggaaaatc atcggtgacg ggagatgggc ccttggtcat taaaagagtg tacaaaggtg gtgcggctga acaagctgga
```

```
                      -continued
ataatagaag ctggagatga aattcttgct attaatggga aacctctggt tgggctcatg cactttgatg cctggaatat tatgaagtct gtcccagaag gacctgtgca gttattaatt agaaagcata ggaattctt ca
```

The sPDZD2 gene, or the protein, of the present invention can be obtained from human tissue or synthesized using a conventional DNA or peptide synthesis method. Further, the gene thus prepared may be inserted into a conventional vector to obtain an expression vector, which may, in turn, be introduced into a suitable host, e.g., a microorganism such as an *E. coli* or yeast, or an animal cell such as a mouse or human cell.

The transformed host may then be used in producing the inventive DNA or protein on a large scale.

The present invention provides a method for suppressing growth of a cancer cell comprising introducing an expression vector containing the inventive sPDZD2 gene into a cancer cell to induce antiproliferation and/or apoptosis thereof. Any type of cancer cell may be used in the inventive method. Preferred are cervical, prostate, pancreatic, kidney, sarcoma, leukemia, lymphoma, liver, uterine, colon, lung, brain, ovarian and breast cancer cells, and more preferred is a prostate cancer cell.

The present invention also includes within its scope a pharmaceutical composition for treating or preventing cancer which comprises the inventive tumor suppressor gene as an active ingredient and pharmaceutically acceptable carriers, excipients or other additives, if necessary. The pharmaceutical composition of the present invention is preferably formulated for administration by injection with a diluent (such as normal saline, distilled water, or other aqueous vehicle with or without preservatives or other inactive ingredients) for example.

The pharmaceutical composition of the present invention is administered into a cancerous tissue of a subject in a conventional manner to slow the growth of the tissue. The amount of the tumor suppressor gene actually administered should be determined in light of various relevant factors including the condition to be treated, the chosen route of administration, the age and weight of the individual patient, and the severity of the patient's symptoms.

The invention further provides a tumor suppressor protein, a pharmaceutical composition comprising the tumor suppressor protein, together with a pharmaceutically acceptable vehicle and a method for suppressing or inhibiting tumor cell growth comprising administering an effective amount of the tumor suppressor protein in a pharmaceutically effective vehicle.

The following Examples are intended to further illustrate the present invention without limiting its scope.

EXAMPLE 2

Figure 1B:
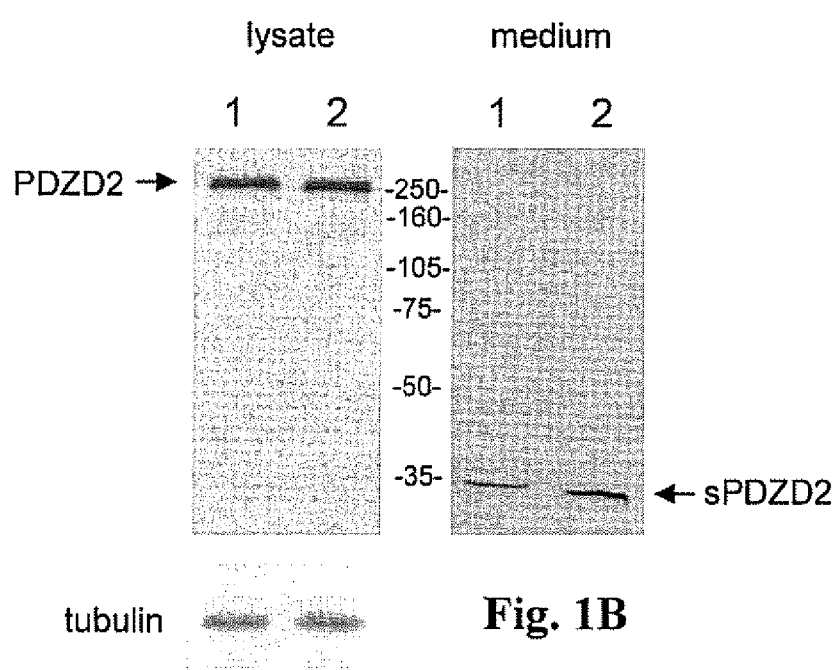
FIG. 1B shows the expression and secretion of PDZD2/sPDZD2 in breast and liver cancer cells. The presence of PDZD2 and sPDZD2 in cell lysates and concentrated conditioned media of (Lane 1) Hep-G2 and (Lane 2) MCF-7 cells were detected by immunoblotting, using rabbit anti-PDZD2 antiserum (1:10,000 dilution).
Figure 1C:
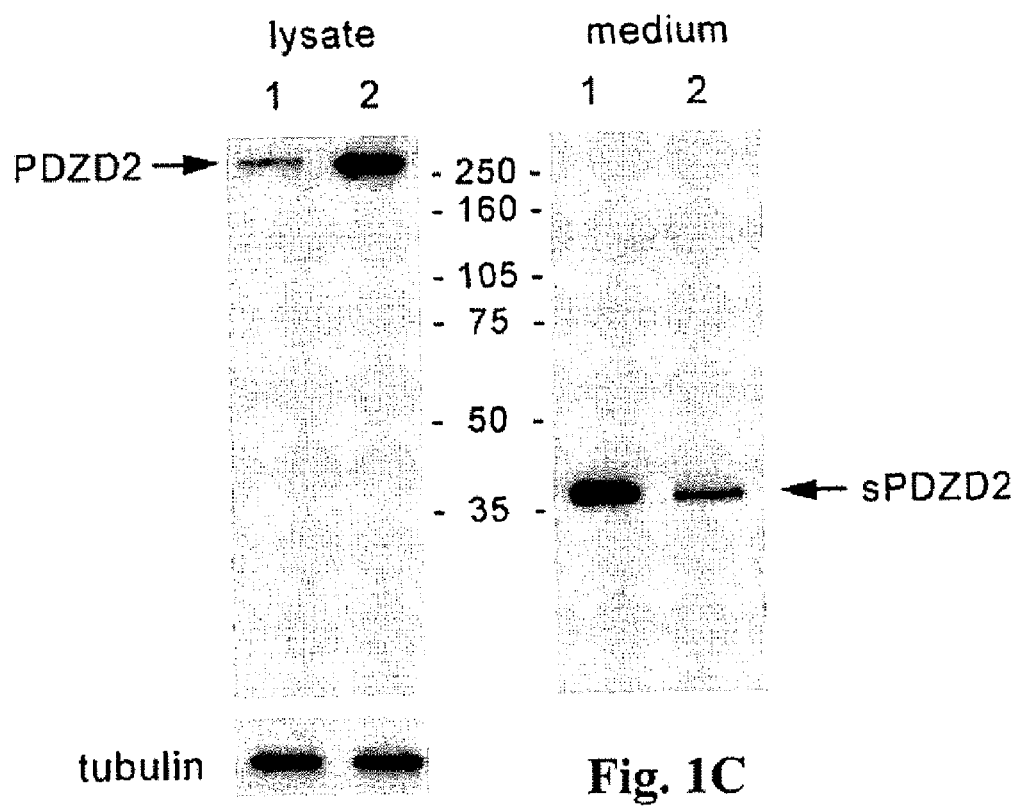
FIG. 1C shows the effects of caspase-3 inhibitor Z-DEVD-FMK on PDZD2/sPDZD2 expression and secretion. DU145 cells were treated with (Lane 1) 10 $\mu$M Z-FA-FMK (an inactive analog of Z-DEVD-FMK), or (Lane 2) 10 $\mu$M Z-DEVD-FMK for 48 hours. Cell lysates were harvested and the conditioned media were concentrated before detection of PDZD2 and sPDZD2 using rabbit anti-PDZD2 antiserum (1:10,000 dilution).
Figure 1D:
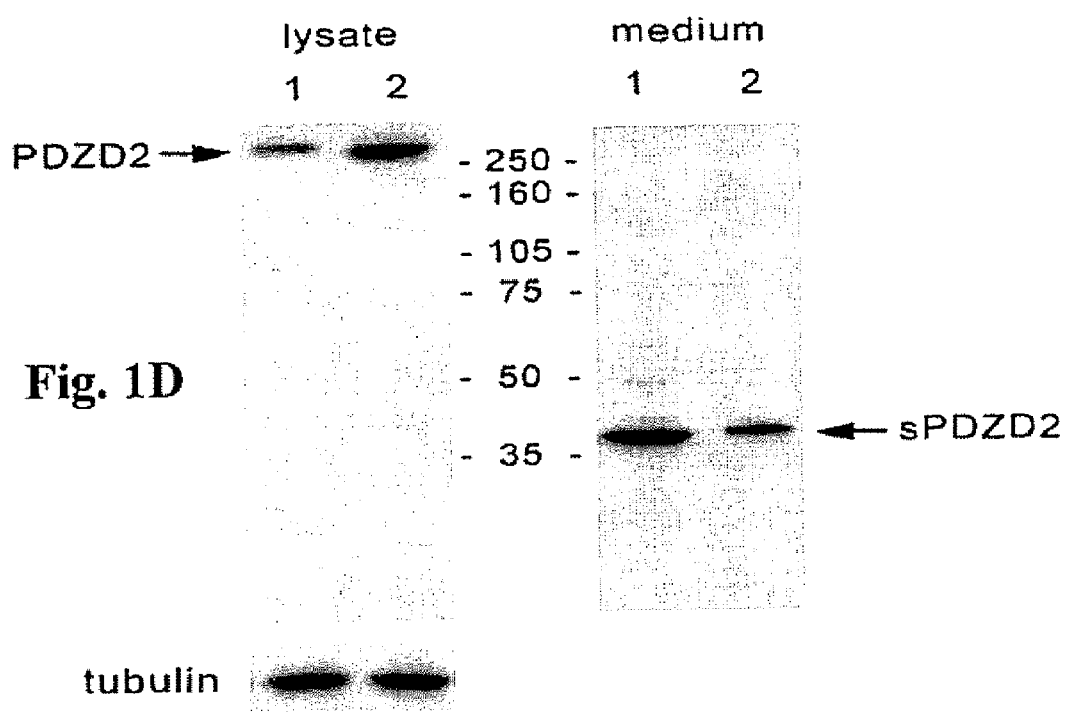
FIG. 1D shows the effects of caspase-3 inhibitor Z-DEVD-FMK on PDZD2/sPDZD2 expression and secretion. PC-3 cells were treated with (Lane 1) 10 $\mu$M Z-FA-FMK (an inactive analog of Z-DEVD-FMK), or (Lane 2) 10 $\mu$M Z-DEVD-FMK for 48 hours. Cell lysates were harvested and the conditioned media were concentrated before detection of PDZD2 and sPDZD2 using rabbit anti-PDZD2 antiserum (1:10,000 dilution).
Figure 1E:
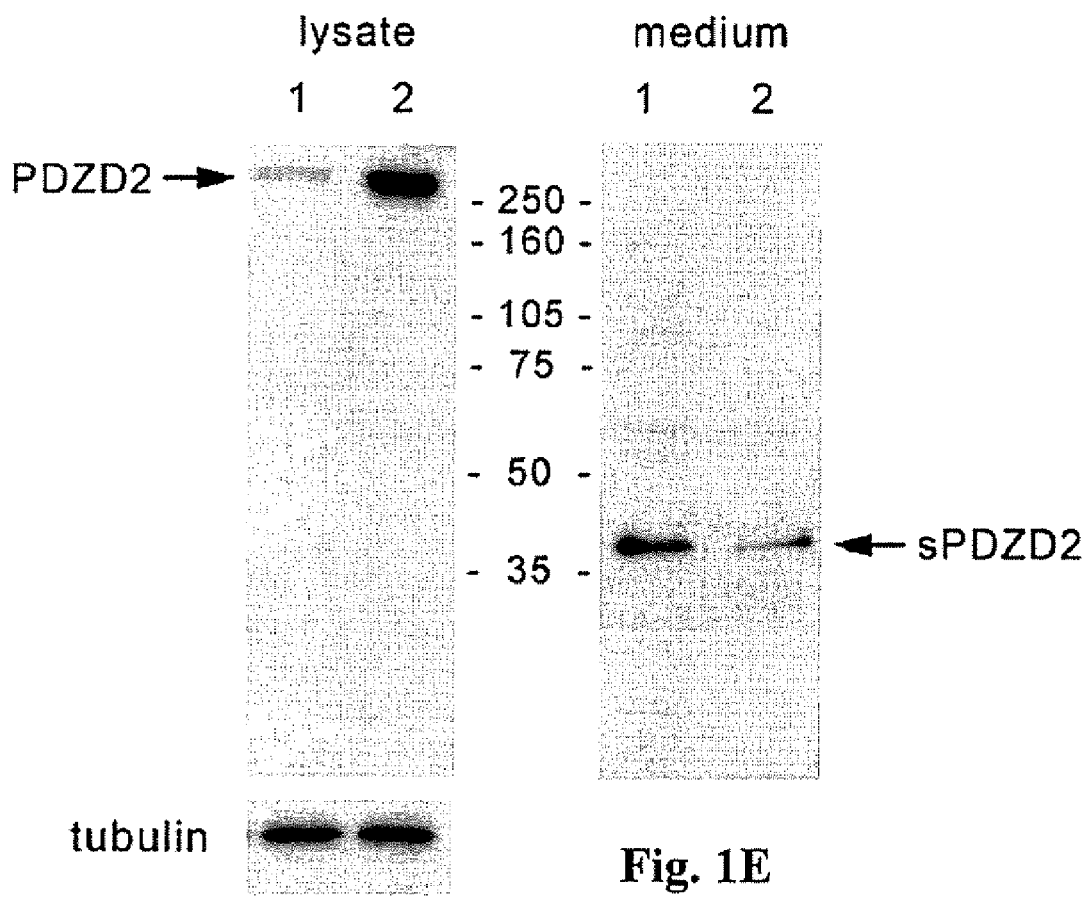
FIG. 1E shows the effects of caspase-3 inhibitor Z-DEVD-FMK on PDZD2/sPDZD2 expression and secretion. 22Rv1 cells were treated with (Lane 1) 10 $\mu$M Z-FA-FMK, (an inactive analog of Z-DEVD-FMK), or (Lane 2) 10 $\mu$M Z-DEVD-FMK for 48 hours. Cell lysates were harvested and the conditioned media were concentrated before detection of PDZD2 and sPDZD2 using rabbit anti-PDZD2 antiserum (1:10,000 dilution).
Figure 1F:
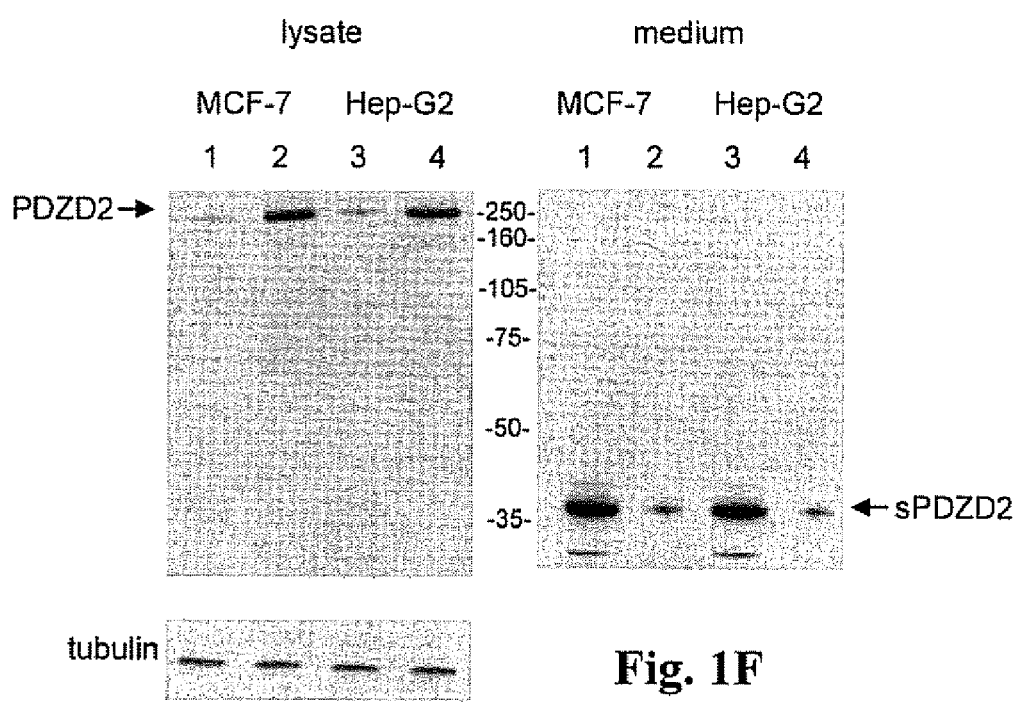
FIG. 1F shows the effects of caspase-3 inhibitor Z-DEVD-FMK on PDZD2/sPDZD2 expression and secretion. MCF-7 and Hep-G2 cells were treated with (Lanes 1 and 3) 10 $\mu$M Z-FA-FMK, (an inactive analog of Z-DEVD-FMK), or (Lanes 2 and 4) 10 $\mu$M Z-DEVD-FMK for 48 hours. Cell lysates were harvested and the conditioned media were concentrated before detection of PDZD2 and sPDZD2 using rabbit anti-PDZD2 antiserum (1:10,000 dilution).
Figure 1G:
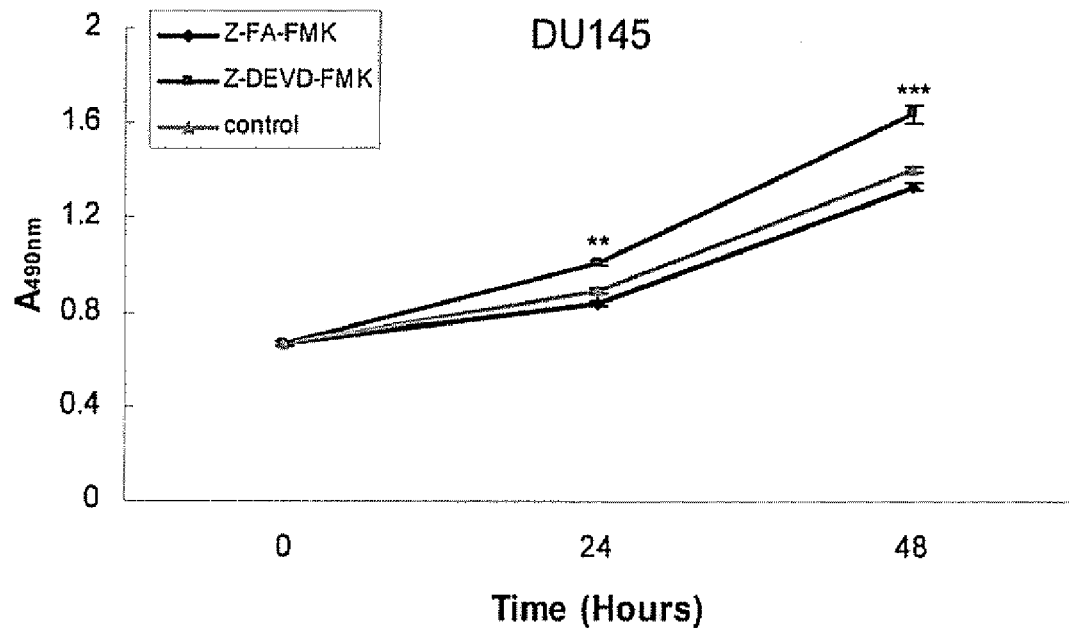
FIG. 1G shows the effects of caspase-3 inhibitor Z-DEVD-FMK on cell growth. DU145 cells were treated with 10 μM Z-DEVD-FMK, 10 μM Z-FA-FMK, or vehicle for 24 and 48 hours. Cell proliferation was monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. P<0.01 and *P<0.001 compared to control.
Figure 1H:
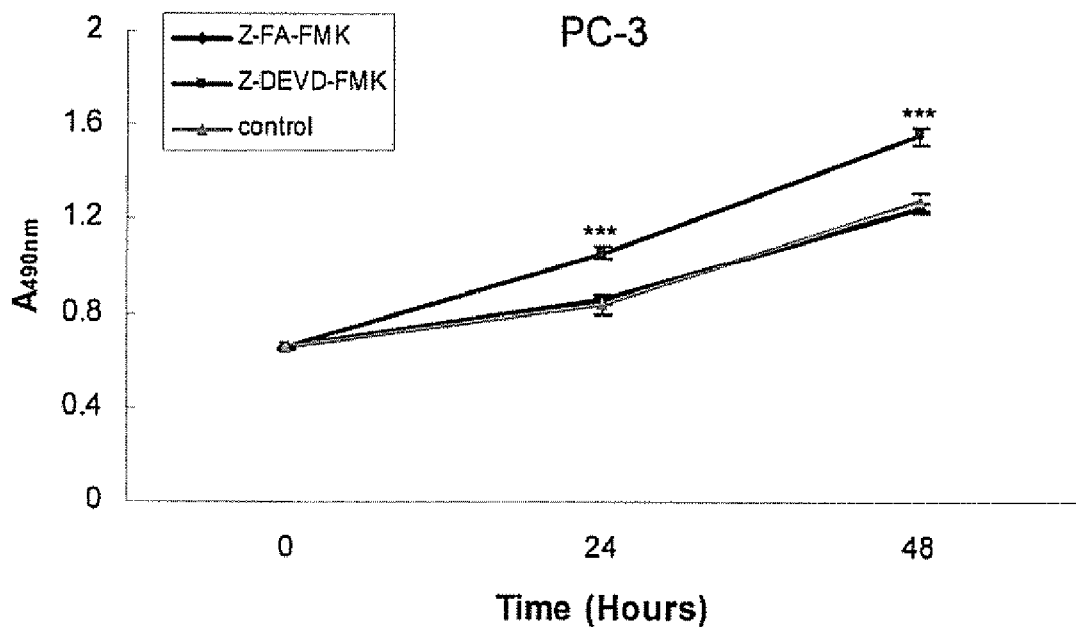
FIG. 1H shows the effects of caspase-3 inhibitor Z-DEVD-FMK on cell growth. PC-3 cells were treated with 10 μM Z-DEVD-FMK, 10 μM Z-FA-FMK, or vehicle for 24 and 48 hours. Cell proliferation was monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. ***P<0.001 compared to control.
Figure 1I:
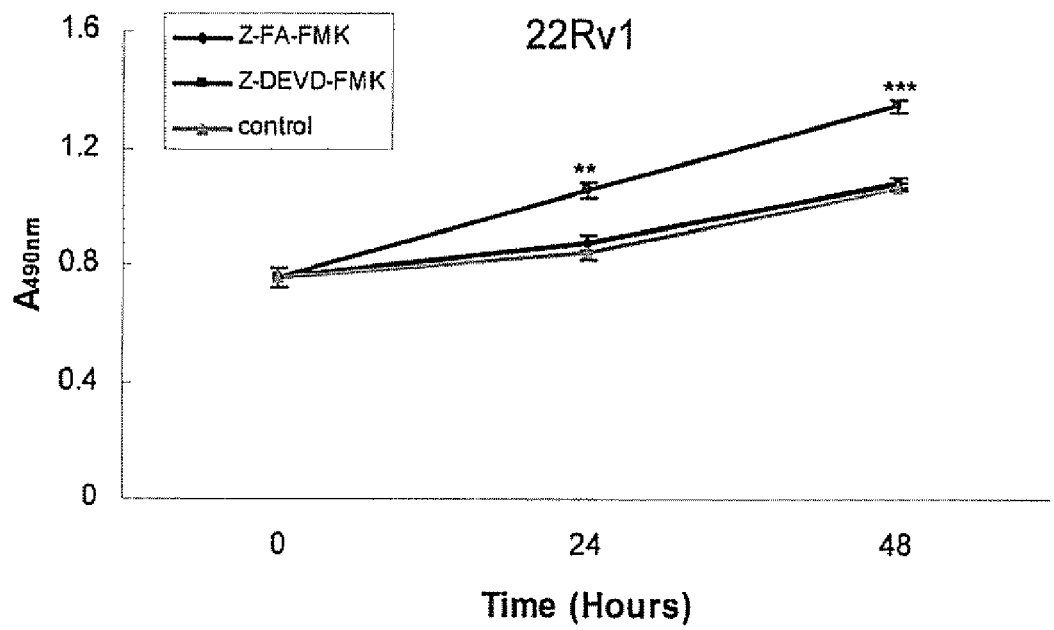
FIG. 1I shows the effects of caspase-3 inhibitor Z-DEVD-FMK on cell growth. 22Rv1 cells were treated with 10 μM Z-DEVD-FMK, 10 μM Z-FA-FMK, or vehicle for 24 and 48 hours. Cell proliferation was monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. P<0.01 and *P<0.001 compared to control.
Figure 1J:
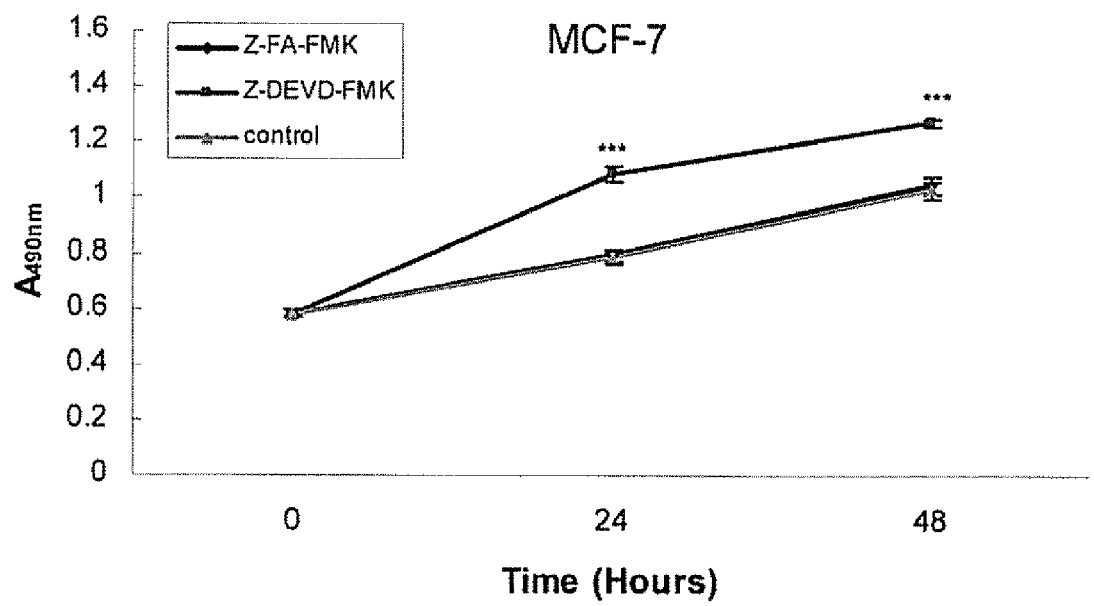
FIG. 1J shows the effects of caspase-3 inhibitor Z-DEVD-FMK on cell growth. MCF-7 cells were treated with 10 μM Z-DEVD-FMK, 10 μM Z-FA-FMK, or vehicle for 24 and 48 hours. Cell proliferation was monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. ***P<0.001 compared to control.
Figure 1K:
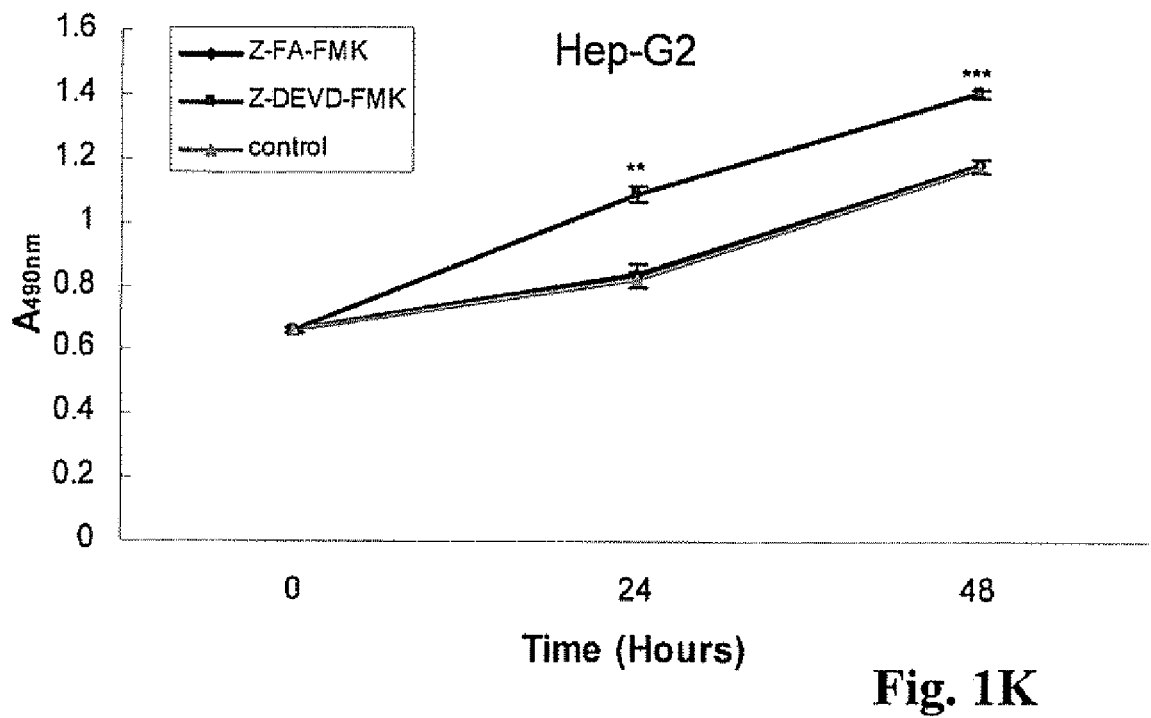
FIG. 1K shows the effects of caspase-3 inhibitor Z-DEVD-FMK on cell growth. Hep-G2 cells were treated with 10 μM Z-DEVD-FMK, 10 μM Z-FA-FMK, or vehicle for 24 and 48 hours. Cell proliferation was monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. P<0.01 and *P<0.001 compared to control.

Endogenous PDZD2 Expression and sPDZD2 Secretion in Prostate, Breast and Liver Cancer Cells Using a specific anti-PDZD2 antiserum that recognize both the full-length and secreted forms of PDZD2, we analyzed the lysates and conditioned media from cultured DU145, PC-3, 22Rv1, LNCaP, MCF-7 and Hep-G2 cells by immunoblotting. PBS-washed native prostate, breast and liver cancer cells were incubated in their respective culture media without any added FBS for 24 hours, before the cells and conditioned media were collected for immunoblotting with the rabbit anti-PDZD2 antibody. Full-length PDZD2 (301 kDa) and sPDZD2 (37 kDa) were detected, respectively, in the cell lysates and conditioned media of all cancer cell lines. The lack of detectable expression of sPDZD2 in the cell lysates suggests that sPDZD2 is predominantly secreted rather than stored intracellularly after its cleavage from PDZD2 (FIGS. 1A and 1B).

EXAMPLE 3

Construction, Expression and Purification of Recombinant Human sPDZD2 Protein

Human sPDZD2 cDNA was amplified by PCR with a sense primer: 5'-GTT-GTT-cat-atg-CTT-GAC-AAG-CTC-TGC-AGC-GAG-GAT-3' (SEQ ID NO:3) and an anti-sense primer: 5'-GTT-GTT-ctc-gag-TCA-TGA-AGA-ATT-CCT-ATG-CTT-TCT-AAT-TAA-3' (SEQ ID NO:4). The 5' ends of the sense and anti-sense amplimers were tagged with the restriction enzyme sequences of NdeI and XhoI respectively to facilitate subsequent subcloning of amplified human sPDZD2 cDNA into the expression vector pTYBI2. PCR was performed using the Advantage® 2 PCR Kit (Clontech), in a 50 µl reaction mixture contained 5 µl Advantage® 2 PCR buffer [40 mM Tricine-KOH (pH 8.7), 15 mM KOAc, 3.5 mM Mg(OAc)$_2$, 3.75 µg/ml BSA, 0.005% Tween 20, 0.005% NP-40], 5 µl dNTPs (10 mM each), 0.5 µl of each primer (100 pmole/µl), 1 ng KIAA0300 cDNA, and 1 µl Advantage® 2 polymerase mix. The 25 cycles of PCR amplification were preceded by a heat-denaturing step at 94° C. for 105 seconds. Each PCR cycle consisted of denaturation at 94° C. for 10 seconds, annealing at 68° C. for 30 seconds and extension at 68° C. for 60 seconds. The specific PCR product was then digested with NdeI and XhoI before gel electrophoresis and purification. The digested and purified sPDZD2 cDNA was ligated with NdeI and XhoI digested pTYB12 vector DNA before transformation into competent DE-15a bacterial cells. The plasmid DNA pTYBI2-sPDZD2 was finally sequenced in both directions.

The IMPACT™ (Intein Mediated Purification with an Affinity Chitin-binding Tag)-CN system from New England Biolabs was used for the synthesis of recombinant human sPDZD2 protein. This system utilizes the inducible self-cleavage activity of intein to separate the target protein from the affinity tag. The pTYB12-sPDZD2 construct was transformed into the bacterial host strain ER2566 and the recombinant sPDZD2 protein was synthesized according to the manufacturer's instructions. Briefly, the production of the intein-sPDZD2 fusion protein was carried out by induction using 0.75 mM IPTG at 28° C. for 6 hours with constant shaking. Cells were then harvested and resuspended in column buffer [20 mM Tris-HCl (pH 8.0), 500 mM NaCl, and 1 mM EDTA, with protease inhibitors]. After sonication for 10 minutes with approximately 10 seconds per pulse to release cellular proteins, cell debris was removed by centrifugation at 4000 rpm at 4° C. for 10 minutes, followed by centrifugation at 16000 rpm at 4° C. for 15 minutes. Supernatant fluid containing the intein-sPDZD2 recombinant protein was filtered through 0.45 µm filter and then slowly loaded onto an equilibrated chitin column. The collected flow through portion was repeatedly loaded onto the column to ensure maximal binding. The column was subsequently washed extensively by using column buffer and on-column self-cleavage of the intein portion was induced at room temperature in the presence of cleavage buffer (50 mM DTT in column buffer) for 30 hours. Finally, the eluant was collected, followed by dialysis in 20 mM Tris-HCl (pH 8.0), 1 mM EDTA buffer and concentrated by YM-10 centricons.

The amino acid sequence (one letter amino acid code) of recombinant human sPDZD2 protein (SEQ ID NO:5) is listed (amino acids AGH (in italics) at the N-terminus of recombinant human sPDZD2 protein are encoded by pTYB 12 expression vector sequences) as follows:

(SEQ ID NO: 5)
AGHLDKLCSEDYSAGPSAVLFKTELEITPRRSPGPPAGGVSCPEKGGNRA

CPGGSGPKTSAAETPSSASDTGEAAQDLPFRRSWSVNLDQLLVSAGDQQR

LQSVLSSVGSKSTILTLIQEAKAQSENEEDVCFIVLNRKEGSGLGFSVAG

GTDVEPKSITVHRVFSQGAASQEGTMNRGDFLLSVNGASLAGLAHGNVLK

VLHQAQLHKDALVVIKKGMDQPRPSARQEPPTANGKGLLSRKTIPLEPGI

GRSVAVHDALCVEVLKTSAGLGLSLDGGKSSVTGDGPLVIKRVYKGGAAE

QAGIIEAGDEILAINGKPLVGLMHFDAWNIMKSVPEGPVQLLIRKHRNSS

EXAMPLE 4

Effects of Caspase-3 Inhibitor Z-DEVD-FMK on Endogenous PDZD2 Expression and sPDZD2 Secretion, and Cancer Cell Growth Full-length PDZD2 protein, which exhibits close sequence homology to pro-IL-16, is processed and cleaved by a caspase-dependent mechanism to generate sPDZD2. Given that cleavage of pro-IL-16 to form the corresponding secretory IL-16 cytokine is mediated by caspase-3, we tested whether or not proteolytic cleavage of full-length PDZD2 to its secreted protein sPDZD2 is caspase-3-dependent in human prostate, breast and liver cancer cells. Human prostate cancer cell lines LNCaP.FGC (CRL-1740), DU145 (HTB-81), PC-3 (CRL-1435), and 22Rv1 (CRL-2505), breast adenocarcinoma cell line MCF-7 (HTB-22), and hepatocellular carcinoma cell line Hep-G2 (HB-8065) were obtained from American Type Culture Collection. DU145, PC-3, 22Rv1, MCF-7, and Hep-G2 cells were incubated under serum-free conditions for 48 hours with either 10 µM Z-DEVD-FMK (BD Biosciences), a specific inhibitor of caspase-3, or 10 µM Z-FA-FMK (BD Biosciences), a negative control peptide, before the cells and conditioned media were collected for immunoblotting with the rabbit anti-PDZD2 antibody. Cell lysates in sample buffer (0.2% SDS, 10% glycerol, 0.06 M Tris-HCl (pH 6.8), 100 mM DTT, and 0.01% bromophenol blue) were heated at 95° C. for 5 min. Proteins in the conditioned media were concentrated by 50-fold using YM-10 Centricons (Millipore). Samples (10 µg) were resolved by SDS-PAGE and electroblotted to PVDF membranes (Millipore). The blots were blocked with 5% non-fat milk powder in TBS-T for 1 hour at room temperature and then incubated with rabbit anti-PDZD2 antibody (1:10,000 dilution) overnight at 4° C. After washing with TBS-T, the blots were incubated with secondary antibodies against rabbit immunoglobulin G (ZYMED Laboratories). Blots were stripped in 25 mM glycine buffer (pH 2.0) for 30 min for re-probing with α-tubulin (1:500 dilution, Santa Cruz Biotechnology). The signals were visualized by enhanced chemiluminescence Western blotting system (Amersham Biosciences) and densitometric scannings of films of the developed blot normalized against α-tubulin were determined. Treatment of DU145, PC-3, 22Rv1, MCF-7 and Hep-G2 cells with Z-DEVD-FMK for 48 hours resulted in 40%, 28%, 44%, 57% and 52% reduction of sPDZD2 secretion into the respective conditioned media, as compared to cells treated with Z-FA-FMK. Concomitantly, PDZD2 expression in DU145, PC-3, 22Rv1, MCF-7 and Hep-G2 cells showed a respective 3-fold, 2-fold, 4.4-fold, 3.5-fold and 4.1-fold increase, as compared to Z-FA-FMK-treated cells (FIGS. 1C-1F). These data indicated that the proteolytic cleavage of PDZD2 is mediated by caspase-3.

To determine whether or not alterations in PDZD2 and sPDZD2 levels in inhibitor-treated cells are associated with any changes in the cell growth rate, we also monitored DU145, PC-3, 22Rv1, MCF-7 and Hep-G2 cell proliferation by MTS-based assays. Cell proliferation was measured by a tetrazolium-based Cell Titer 96® AQueous assay kit (Promega). Absorbance at 490 nm was recorded 3 hours after MTS addition. There were significant ($P<0.01$) increases in DU145 (20.1% to 22.7%), PC-3 (22.9% to 24.8%), 22Rv1 (23.4% to 26%), MCF-7 (21.5% to 37.2%), and Hep-G2 (19.3% to 30.8%) cell proliferation after the cells were treated with 10 µM of the caspase-3 inhibitor Z-DEVD-FMK for 24 and 48 hours (FIGS. 1G-1K).

Figure 1L:
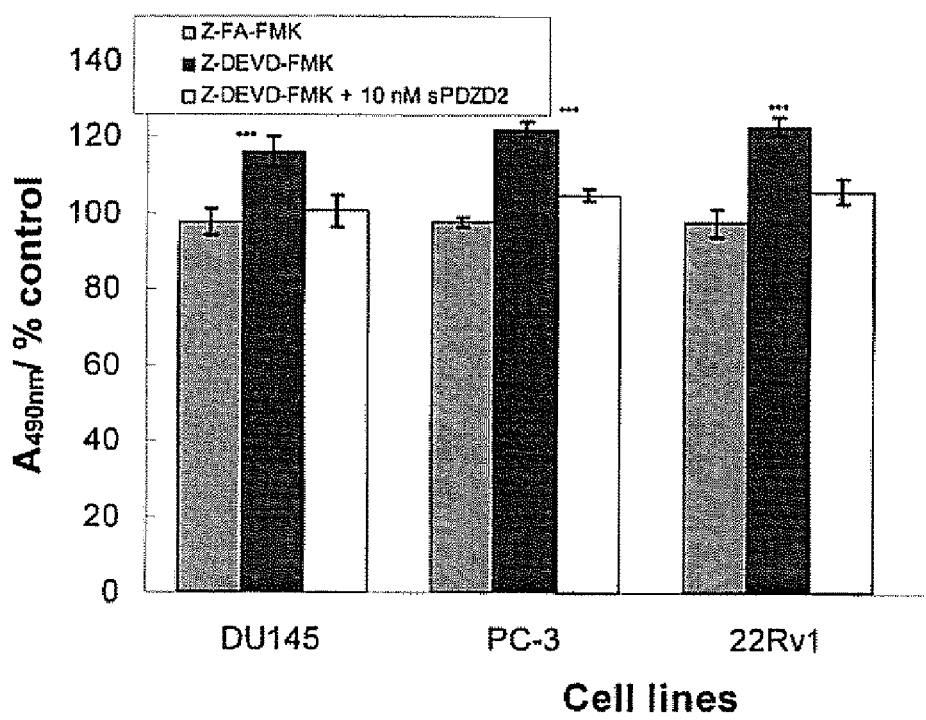
FIG. 1L shows the effects of caspase-3 inhibitor Z-DEVD-FMK with or without exogenous sPDZD2 on cell growth. DU145, PC-3, and 22Rv1 cells were incubated with 10 μM Z-DEVD-FMK, 10 μM Z-FA-FMK, 10 μM Z-DEVD-FMK plus 10-8 M sPDZD2, or vehicle for 48 hours. Cell proliferation was monitored by MTS assays. Data are shown as mean.±.S.E. Two group comparisons were analyzed by unpaired Student's t test. The level of significance for all statistical analyses was set at P<0.05. ***P<0.001 compared to control.
Figure 1M:
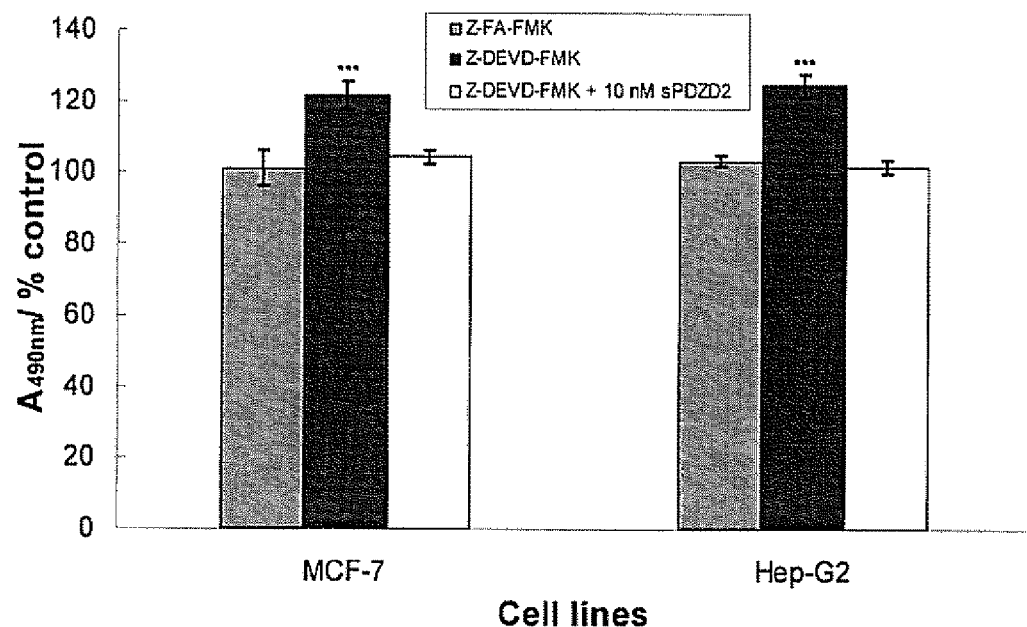
FIG. 1M shows the effects of caspase-3 inhibitor Z-DEVD-FMK with or without exogenous sPDZD2 on cell growth. MCF-7 and Hep-G2 cells were incubated with 10 μM Z-DEVD-FMK, 10 μM Z-FA-FMK, 10 μM Z-DEVD-FMK plus $10^{-8}$ M sPDZD2, or vehicle for 48 hours. Cell proliferation was monitored by MTS assays. Data are shown as mean.±.S.E. Two group comparisons were analyzed by unpaired Student's t test. The level of significance for all statistical analyses was set at P<0.05. ***P<0.001 compared to control.
Figure 2A:
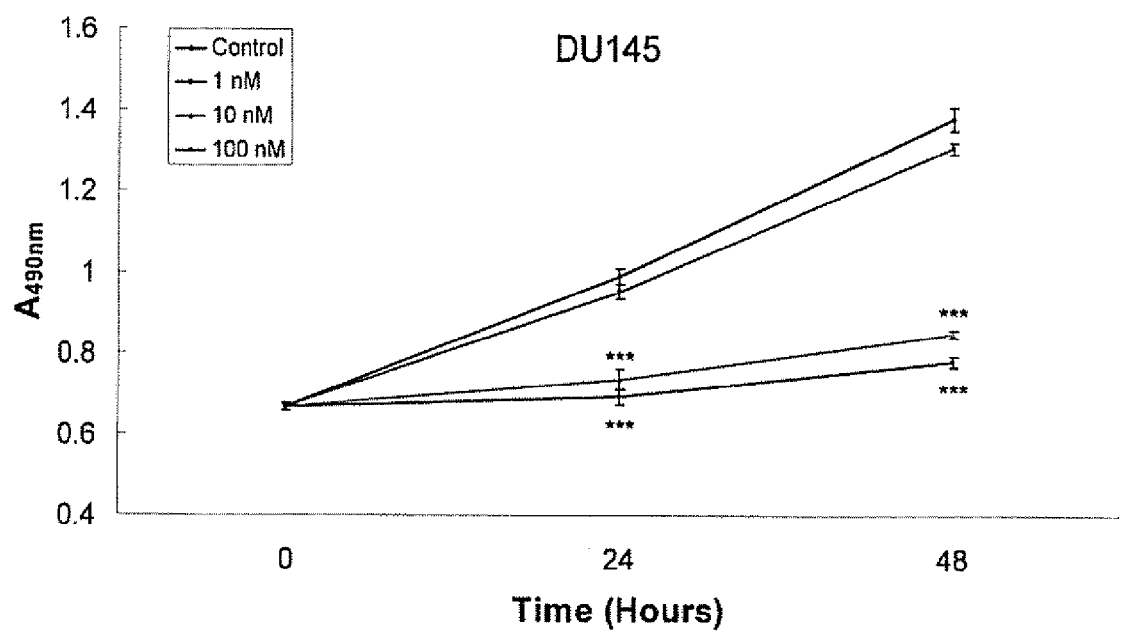
FIG. 2A shows the effects of sPDZD2 on prostate cancer cell proliferation. DU145 cells were treated with $10^{-9}$ M, $10^{-8}$ M, and $10^{-7}$ M recombinant sPDZD2 for 24 and 48 hours. The effects of sPDZD2 on cell proliferation were monitored by MTS assays. Data are shown as mean.±S.E. The data were analyzed with one way ANOVA followed by Tukey's test. Two group comparisons were analyzed by unpaired Student's t test. The level of significance for all statistical analyses was set at P<0.05. ***P<0.001 compared to control.
Figure 2B:
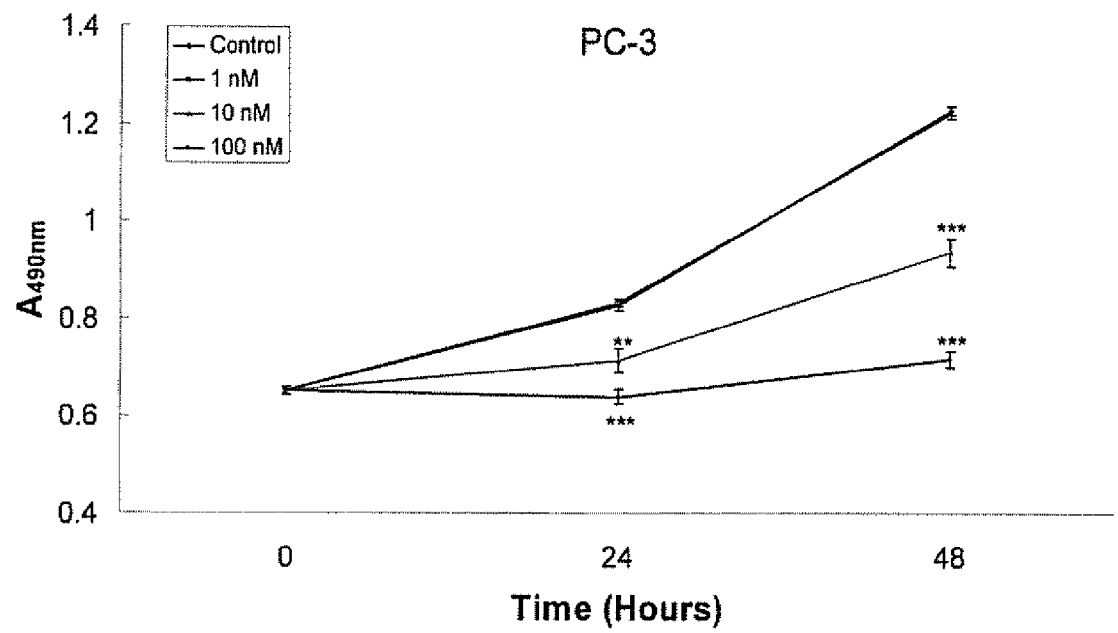
FIG. 2B shows the effects of sPDZD2 on prostate cancer cell proliferation. PC-3 cells were treated with $10^{-9}$ M, $10^{-8}$ M, and $10^{-7}$ M recombinant sPDZD2 for 24 and 48 hours. The effects of sPDZD2 on cell proliferation were monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. P<0.01 and *P<0.001 compared to control.
Figure 2C:
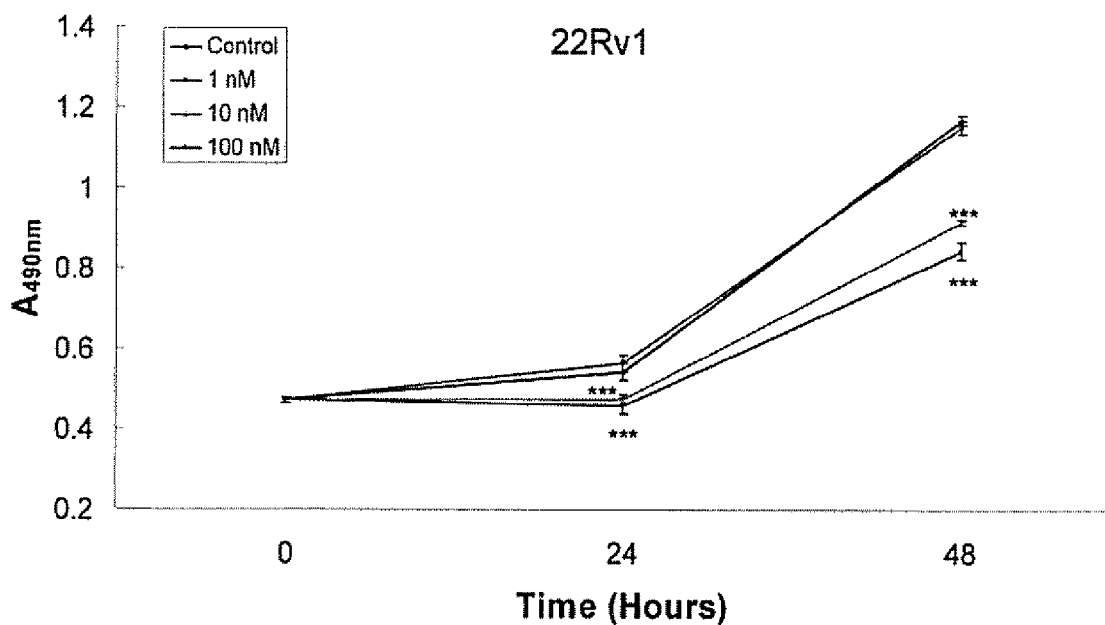
FIG. 2C shows the effects of sPDZD2 on prostate cancer cell proliferation. 22Rv1 cells were treated with $10^{-9}$ M, $10^{-8}$ M, and $10^{-7}$ M recombinant sPDZD2 for 24 and 48 hours. The effects of sPDZD2 on cell proliferation were monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. ***P<0.001 compared to control.
Figure 2D:
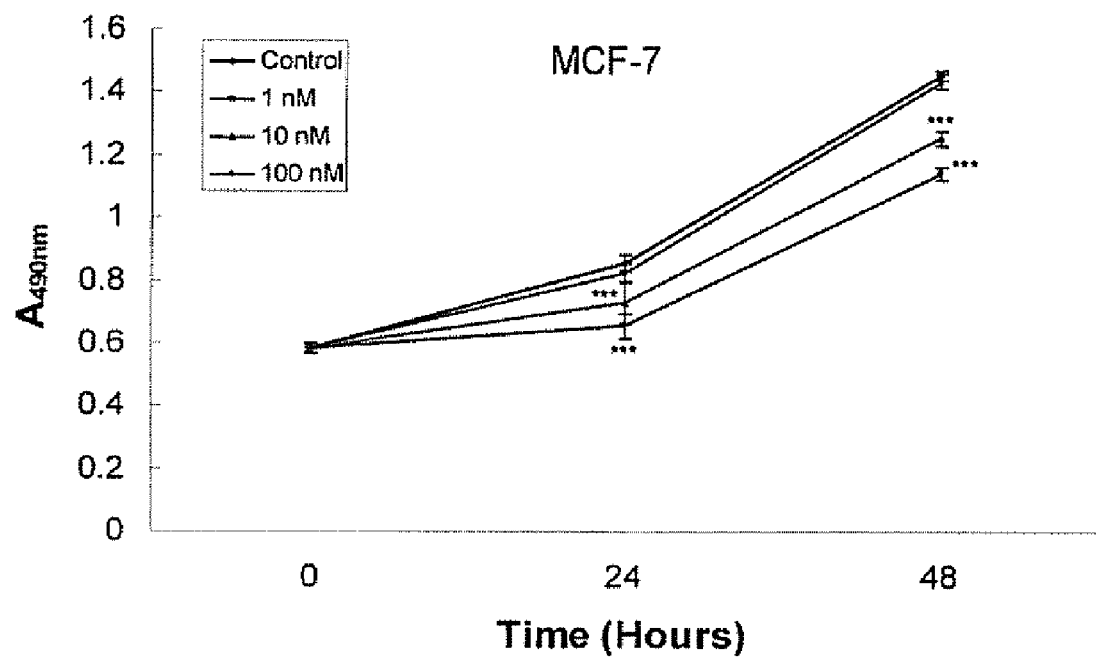
FIG. 2D shows the effects of sPDZD2 on breast cancer cell proliferation. MCF-7 cells were treated with $10^{-9}$ M, $10^{-8}$ M, and $10^{-7}$ M recombinant sPDZD2 for 24 and 48 hours. The effects of sPDZD2 on cell proliferation were monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. ***P<0.001 compared to control.
Figure 2E:
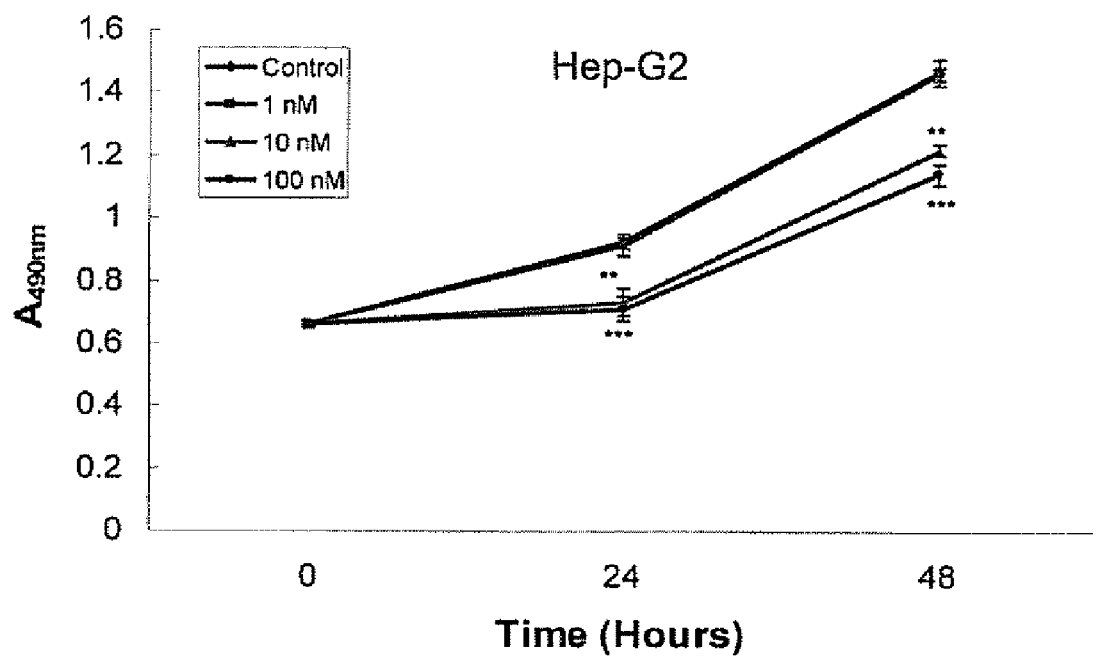
FIG. 2E shows the effects of sPDZD2 on liver cancer cell proliferation. Hep-G2 cells were treated with $10^{-9}$ M, $10^{-8}$ M, and $10^{-7}$ M recombinant sPDZD2 for 24 and 48 hours. The effects of sPDZD2 on cell proliferation were monitored by MTS assays. Data are shown as mean±S.E. The data were analyzed with one way ANOVA followed by Tukey's test. Two group comparisons were analyzed by unpaired Student's t test. The level of significance for all statistical analyses was set at P<0.05. P<0.01 and *P<0.001 compared to control.

To examine if the observed increases in cell proliferation were due to inhibition of sPDZD2 secretion, we tested the ability of exogenously applied recombinant sPDZD2 to counteract the growth-promoting effects of the caspase-3 inhibitor. In separate sets of experiments, DU145, PC-3, 22Rv1, MCF-7 and Hep-G2 cells were incubated with 10 µM specific caspase-3 peptide inhibitor, Z-DEVD-FMK (BD Biosciences), 10 µM negative control peptide Z-FA-FMK (BD Biosciences), or vehicle for 48 hours. In addition, DU145, PC-3, 22Rv1, MCF-7 and Hep-G2 cells were each co-incubated with 10 µM Z-DEVD-FMK and $10^{-8}$ M sPDZD2 for 48 hours. As shown in FIGS. 1L and 1M, the increases in DU145, PC-3, 22Rv1, MCF-7 and Hep-G2 cell proliferation induced by caspase-3 inhibitor treatment were abolished by co-incubating with $10^{-8}$ M sPDZD2. These results suggest that the antiproliferative effects were predominantly mediated by sPDZD2 instead of PDZD2.

EXAMPLE 5

Effects of Recombinant sPDZD2 on Cancer Cell Growth In Vitro and In Vivo

For in vitro studies, DU145, PC-3, 22Rv1, MCF-7 and Hep-G2 cells ($2\times10^4$/ml) were seeded in 96-well plates and were incubated with or without $10^{-9}$ M, $10^{-8}$ M, and $10^{-7}$ M purified recombinant sPDZD2, or vehicle (20 mM Tris-HCl, pH 8, 1 mM EDTA) for 24 and 48 hours before the cells were processed for cell proliferation studies. Cell proliferation was measured by a tetrazolium-based Cell Titer 96® AQueous assay kit (Promega). Absorbance at 490 nm was recorded 3 hours after MTS addition. Cell viabilities of DU145, PC-3, 22Rv1, MCF-7 and Hep-G2 cells, incubated with or without $10^{-9}$ M, $10^{-8}$ M, and $10^{-7}$ M purified recombinant sPDZD2 for 24 and 48 hours, were measured by trypan blue dye exclusion assays. The number of viable cells was counted using hemocytometers. Any apoptotic effect on cancer cells induced by sPDZD2 was measured by the Cell Death Detection ELISA$^{PLUS}$ assay kit (Roche), which detects the presence of mono- and oligonucleosomes in the cytoplasm of the cells after lysis. Briefly, the cancer cells ($1\times10^5$/ml) were seeded in 24-well plates and treated with $10^{-8}$ M and $10^{-7}$ M sPDZD2 for 24 hours. After treatment, cells were harvested and any apoptosis was detected according to manufacturer's instructions. Recombinant sPDZD2 induced a significant (P<0.001) concentration-dependent inhibition of cell proliferation in DU145, PC-3, 22Rv1, MCF-7 and Hep-G2 cells (FIGS. 2A-2E). Treatment of DU145 cells with $10^{-8}$ M and $10^{-7}$ M sPDZD2 for 24 hours resulted in, respectively, 25.8% and 29.9% decreases in cell proliferation (P<0.001). Treatment of PC-3 cells with $10^{-8}$ M and $10^{-7}$ M sPDZD2 for 24 hours resulted in, respectively, 13.5% and 22.6% decreases in cell proliferation (P<0.01). Treatment of 22Rv1 cells with $10^{-8}$ M and $10^{-7}$ M sPDZD2 for 24 hours resulted in, respectively, 12.7% and 15.4% decreases in cell proliferation (P<0.001). Treatment of MCF-7 cells with $10^{-8}$ M and $10^{-7}$ M sPDZD2 for 24 hours resulted in, respectively, 14.5% and 23.2% decreases in cell proliferation (P<0.001). Similar treatment of Hep-G2 cells with $10^{-8}$ M and $10^{-7}$ M sPDZD2 for 24 hours resulted in, respectively, 21% and 23.1% decreases in cell proliferation (P<0.01). On the other hand, DU145 cell proliferation exhibited 38.6% and 43.5% decreases (P<0.001) after the cells were treated with $10^{-8}$ M and $10^{-7}$ M sPDZD2, respectively, for 48 hours. PC-3 cell proliferation exhibited 23.8% and 41.6% decreases (P<0.001) after the cells were treated with $10^{-8}$ M and $10^{-7}$ M sPDZD2, respectively, for 48 hours. 22Rv1 cell proliferation exhibited 21.7% and 27.7% decreases (P<0.001) after the cells were treated with $10^{-8}$ M and $10^{-7}$ M sPDZD2, respectively, for 48 hours. Similarly, incubation of MCF-7 cells with $10^{-8}$ M and $10^{-7}$ M sPDZD2 for 48 hours resulted in 13.7% and 21.4% decreases (P<0.001) in cell proliferation respectively. For Hep-G2 cells, 17% and 22.2% decreases (P<0.001) in cell proliferation were, respectively, observed after the cells were treated with $10^{-8}$ M and $10^{-7}$ M sPDZD2 for 48 hours. (FIGS. 2A, 2B, 2C, 2D, and 2E). No changes in DU145, PC-3, 22Rv1, MCF-7 and Hep-G2 cell viability were detected (see Table 1 which shows the effects of recombinant sPDZD2 on the viability of human prostate, breast and liver cancer cell lines).

TABLE 1

Effects of recombinant sPDZD2 on the viability of human prostate, breast and liver cancer cell lines†

| | Control | $10^{-8}$ M sPDZD2 | $10^{-7}$ M sPDZD2 |
|---|---|---|---|
| (A) DU 145 | | | |
| 24 hrs. | 95.02 ± 0.47% | 94.66 ± 0.69% | 93.78 ± 1.06% |
| 48 hrs. | 95.09 ± 0.72% | 95.09 ± 1.02% | 95.25 ± 0.88% |
| (B) PC-3 | | | |
| 24 hrs. | 94.21 ± 0.62% | 95.03 ± 1.00% | 90.86 ± 1.12% |
| 48 hrs. | 97.59 ± 0.44% | 95.49 ± 0.79% | 95.45 ± 0.56% |
| (C) 22Rv1 | | | |
| 24 hrs. | 96.81 ± 0.39% | 96.01 ± 0.38% | 96.04 ± 0.50% |
| 48 hrs. | 94.66 ± 0.44% | 93.02 ± 0.47% | 92.65 ± 0.48% |
| (D) MCF-7 | | | |
| 24 hrs. | 97.06 ± 0.49% | 96.69 ± 0.50% | 97.34 ± 0.42% |
| 48 hrs. | 93.67 ± 0.31% | 93.86 ± 0.76% | 92.07 ± 0.89% |
| (E) Hep-G2 | | | |
| 24 hrs. | 93.78 ± 0.31% | 93.38 ± 0.54% | 93.37 ± 0.54% |
| 48 hrs. | 94.82 ± 0.28% | 93.64 ± 0.66% | 93.58 ± 0.64% |

†(A) DU 145, (B) PC-3, (C) 22Rv1, (D) MCF-7, and (E) Hep-G2 cells were incubated with $10^{-8}$ M or $10^{-7}$ M recombinant sPDZD2 for 24 and 48 hours. After treatment, the cells were harvested by trypsinization (0.25%, w/v) and collected by centrifugation at 180 × g for 5 minutes. The viability of the cells was measured by trypan blue exclusion assays. Data shown are mean ± S.E.

Figure 3A:
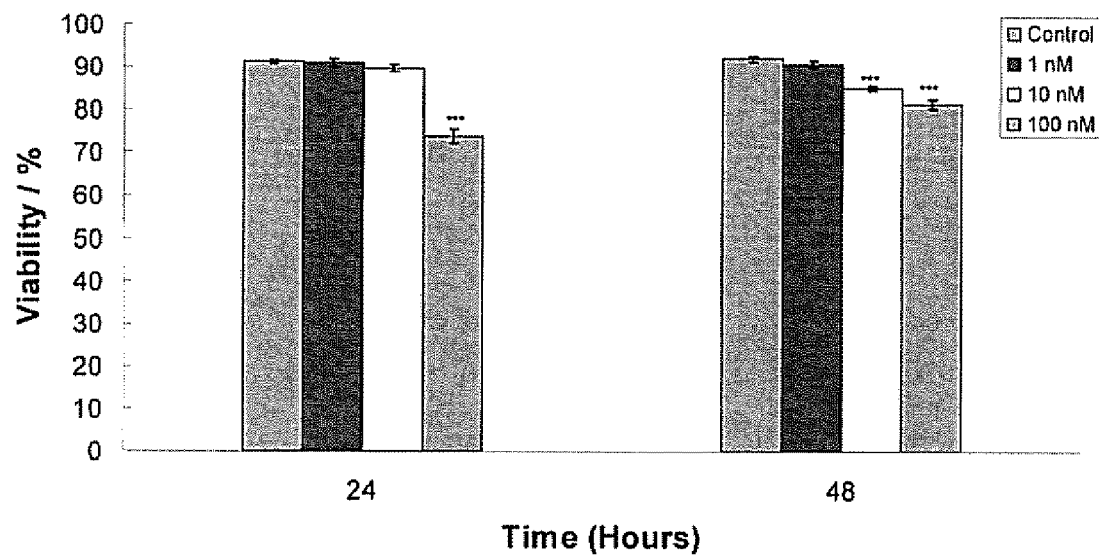
FIG. 3A shows the effects of sPDZD2 on LNCaP cell growth. LNCaP cells were treated with $10^{-9}$ M, $10^{-8}$ M, and $10^{-7}$ M recombinant sPDZD2 for 24 and 48 hours. The effects of sPDZD2 on cell viability were monitored by trypan blue dye exclusion assays. Data are shown as mean±S.E. Two group comparisons were analyzed by unpaired Student's t test. The level of significance for all statistical analyses was set at P<0.05. ***P<0.001 compared to control.
Figure 3B:
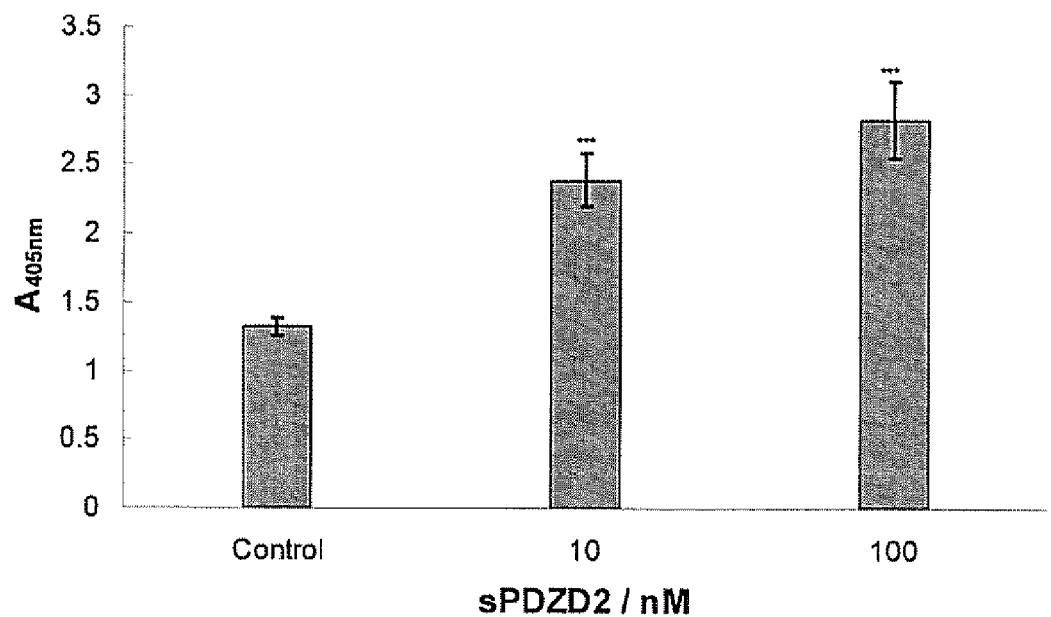
FIG. 3B shows the effects of sPDZD2 on LNCaP cell growth. Cell Death Detection ELISA$^{PLUS}$ assay kit (Roche) was used to determine the apoptotic effects of sPDZD2 on LNCaP cells. After treatment of the cells with $10^{-8}$ M and $10^{-7}$ M recombinant sPDZD2 for 24 hours, the cells were lysed and the presence of nucleosomes in the cytoplasm was detected by measuring absorbance values at 405 nm. Data are shown as mean±S.E. Two group comparisons were analyzed by unpaired Student's t test. The level of significance for all statistical analyses was set at P<0.05. ***P<0.001 compared to control.

In contrast, incubation of LNCaP cells with $10^{-7}$ M sPDZD2 for 24 hours resulted in 26.2% decrease in cell viability (P<0.001), whereas LNCaP cell viability exhibited 14.7% and 18.6% decreases (P<0.001) after treatment with $10^{-8}$ M and $10^{-7}$ M sPDZD2, respectively, for 48 hours (FIG. 3A). The observed decreases in LNCaP cell viability in response to sPDZD2 were found to be due to apoptosis induction (FIG. 3B), as measured by Cell Death Detection ELISA PLUS assay kit (Roche). Significant (P<0.001) increases in absorbance at 405 nm, which reflects an increase in mono- and oligo-nucleosomes in the cell cytoplasm, were observed in LNCaP cells treated with $10^{-8}$ M and $10^{-7}$ M sPDZD2 for 24 hours.

Figure 4:
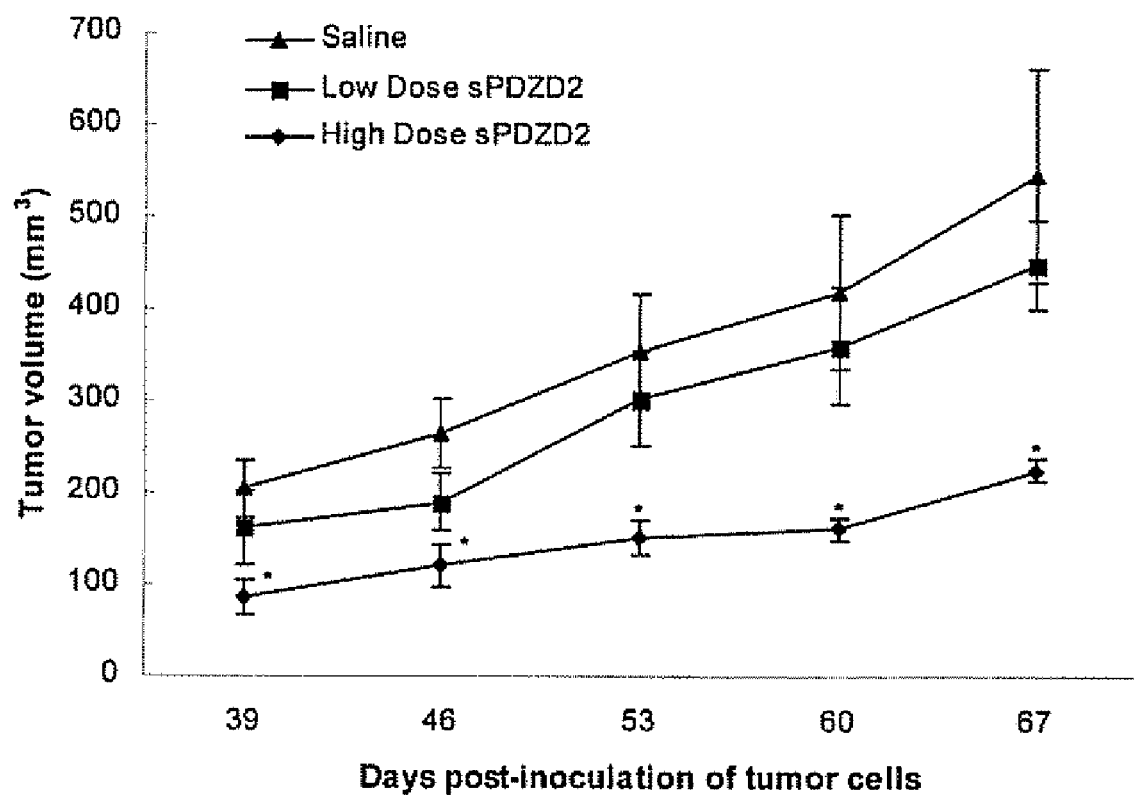
FIG. 4 shows the volume changes of DU145 prostate cancer xenograft tumors in nude mice given daily saline, low dose (0.084 mg recombinant sPDZD2 in 0.1 ml saline/dose/ mouse) or high dose (8.4 mg recombinant sPDZD2 in 0.1 ml saline/dose/mouse) sPDZD2 injections initiated 10 days after inoculation of tumor cells. Data are shown as mean±S.E. Two group comparisons were analyzed by unpaired Student's t test. The level of significance for all statistical analyses was set at P<0.05. *P<0.05 compared to saline-treated control.

For in vivo studies, DU145 cancer cells ($5\times10^6$) in 0.2 ml FBS-containing-EMEM medium were injected subcutaneously into the right flank of each male BALB/c athymic nude mice (weight, 20±2 g). After cancer cell injection, the mice were randomly divided into 3 groups, namely the control, low-dose treatment, and high-dose treatment groups. Ten days after tumor cell implantation, each mouse of the low-dose treatment group and high-dose treatment group was injected, respectively, once daily by the intraperitoneal route with 0.084 mg (in 0.1 ml saline) and 8.4 mg (in 0.1 ml saline) recombinant sPDZD2 for 58 days. The width and length of the tumor in millimeters were measured weekly by a caliper, when the implanted tumor became measurable. The tumor volume was calculated according to the following formula: Volume=$d^2 \times D/2$ mm$^3$, where d is the shorter width and D was the longer length. Changes in tumor volumes in nude mice given daily recombinant sPDZD2 injections are shown in FIG. 4. Compared with saline-treated group, significant decreases (*P<0.05) in tumor volumes were detected in animals treated with high dose recombinant sPDZD2 at 39 days, 46 days, 53 days, 60 days and 67 days after tumor cell implantation. No significant differences were found between tumor volumes of animals treated with low-dose recombinant sPDZD2 and saline-treated group. The tumor growth suppressive function of recombinant human sPDZD2 protein demonstrated in vitro as described above was validated in vivo.

The invention claimed is:

1. A method for inhibiting prostate cancer cell proliferation in a prostate cancer cells comprising:
    administering to the prostate cancer cells an amount of a composition comprising a prostate cancer cell suppressor protein consisting of SEQ ID NO: 1 effective to inhibit prostate cancer cell proliferation.

2. A method for causing prostate cancer cell apoptosis in a prostate cancer cells comprising:
    administering to the prostate cancer cells an amount of a composition comprising a prostate cancer cell suppressor protein consisting of SEQ ID NO: 1 effective to induce prostate cancer cell apoptosis.

3. A method in accordance with claim 1, wherein the composition includes a pharmaceutically acceptable vehicle.

4. A method in accordance with claim 2, where in the composition includes a pharmaceutically acceptable vehicle.

* * * * *

UNITED STATES PATENT AND TRADEMARK OFFICE
CERTIFICATE OF CORRECTION

PATENT NO. : 7,807,626 B2
APPLICATION NO. : 11/761724
DATED : October 5, 2010
INVENTOR(S) : Stephen Yuen Wing Shiu and Kwok Ming Yao It is certified that error appears in the above-identified patent and that said Letters Patent is hereby corrected as shown below:

On the cover page, Column 2, in the Abstract,
line 1, delete "a method for";

Column 3, line 50, "10-8 M" should read --$10^{-8}M$--;

Column 8, line 45, "DE-15A" should read --DH5α--;

Column 8, line 46, "pTYBI2-sPDZD2" should read --pTYB12-sPDZD2--;

In the Claims at column 17, line 54, delete "a"; and

In the Claims at column 17, line 59, delete "a".

Signed and Sealed this
Twenty-eighth Day of December, 2010

David J. Kappos
*Director of the United States Patent and Trademark Office*

SEQUENCE LISTING

<160> NUMBER OF SEQ ID NOS: 5

<210> SEQ ID NO 1
<211> LENGTH: 347
<212> TYPE: PRT
<213> ORGANISM: Human

<400> SEQUENCE: 1

```
Leu Asp Lys Leu Cys Ser Glu Asp Tyr Ser Ala Gly Pro Ser Ala Val
 1               5                  10                  15

Leu Phe Lys Thr Glu Leu Glu Ile Thr Pro Arg Arg Ser Pro Gly Pro
                20                  25                  30

Pro Ala Gly Gly Val Ser Cys Pro Glu Lys Gly Gly Asn Arg Ala Cys
            35                  40                  45

Pro Gly Gly Ser Gly Pro Lys Thr Ser Ala Ala Glu Thr Pro Ser Ser
    50                  55                  60

Ala Ser Asp Thr Gly Glu Ala Ala Gln Asp Leu Pro Phe Arg Arg Ser
65                  70                  75                  80

Trp Ser Val Asn Leu Asp Gln Leu Leu Val Ser Ala Gly Asp Gln Gln
                85                  90                  95

Arg Leu Gln Ser Val Leu Ser Val Gly Ser Lys Ser Thr Ile Leu
                100                 105                 110

Thr Leu Ile Gln Glu Ala Lys Ala Gln Ser Glu Asn Glu Glu Asp Val
            115                 120                 125

Cys Phe Ile Val Leu Asn Arg Lys Glu Gly Ser Gly Leu Gly Phe Ser
    130                 135                 140

Val Ala Gly Gly Thr Asp Val Glu Pro Lys Ser Ile Thr Val His Arg
145                 150                 155                 160

Val Phe Ser Gln Gly Ala Ala Ser Gln Glu Gly Thr Met Asn Arg Gly
                165                 170                 175

Asp Phe Leu Leu Ser Val Asn Gly Ala Ser Leu Ala Gly Leu Ala His
            180                 185                 190

Gly Asn Val Leu Lys Val Leu His Gln Ala Gln Leu His Lys Asp Ala
    195                 200                 205

Leu Val Val Ile Lys Lys Gly Met Asp Gln Pro Arg Pro Ser Ala Arg
210                 215                 220

Gln Glu Pro Pro Thr Ala Asn Gly Lys Gly Leu Leu Ser Arg Lys Thr
225                 230                 235                 240

Ile Pro Leu Glu Pro Gly Ile Gly Arg Ser Val Ala Val His Asp Ala
                245                 250                 255

Leu Cys Val Glu Val Leu Lys Thr Ser Ala Gly Leu Gly Leu Ser Leu
            260                 265                 270

Asp Gly Gly Lys Ser Ser Val Thr Gly Asp Gly Pro Leu Val Ile Lys
    275                 280                 285

Arg Val Tyr Lys Gly Gly Ala Ala Glu Gln Ala Gly Ile Ile Glu Ala
290                 295                 300

Gly Asp Glu Ile Leu Ala Ile Asn Gly Lys Pro Leu Val Gly Leu Met
305                 310                 315                 320

His Phe Asp Ala Trp Asn Ile Met Lys Ser Val Pro Glu Gly Pro Val
                325                 330                 335

Gln Leu Leu Ile Arg Lys His Arg Asn Ser Ser
            340                 345
```

-continued

<210> SEQ ID NO 2
<211> LENGTH: 1041
<212> TYPE: DNA
<213> ORGANISM: Human

<400> SEQUENCE: 2

| | | | | | |
|---|---|---|---|---|---|
| cttgacaagc | tctgcagcga | ggattactca | gcagggccga | gcgccgtgct | cttcaaaact | 60 |
| gagctggaga | tcaccccag | gaggtcacct | ggccctcctg | ctggaggcgt | ttcgtgtccc | 120 |
| gagaagggcg | ggaacagggc | ctgtccagga | ggaagtggcc | ctaaaaccag | tgctgctgag | 180 |
| acacccagtt | cagccagtga | tacgggtgaa | gctgcccagg | atctgccttt | tagaagaagc | 240 |
| tggtcagtta | atttggatca | acttctagtc | tcagcggggg | accagcaaag | attacagtct | 300 |
| gttttatcgt | cagtgggatc | gaaatctacc | atcctaactc | tcattcagga | agcgaaagca | 360 |
| caatcagaga | atgaagaaga | tgtttgcttc | atagtcttga | atagaaaaga | aggctcaggt | 420 |
| ctgggattca | gtgtggcagg | agggacagat | gtggagccaa | aatcaatcac | ggtccacagg | 480 |
| gtgttttctc | aggggcggc | ttctcaggaa | gggactatga | accgagggga | tttccttctg | 540 |
| tcagtcaacg | gcgcctcact | ggctggctta | gcccacggga | atgtcctgaa | ggttctgcac | 600 |
| caggcacagc | tgcacaaaga | tgccctcgtg | gtcatcaaga | aagggatgga | tcagcccagg | 660 |
| ccctctgccc | ggcaggagcc | tcccacagcc | aatgggaagg | gtttgctgtc | cagaaagacc | 720 |
| atcccctgg | agcctggcat | tgggagaagt | gtggctgtac | acgatgctct | gtgtgttgaa | 780 |
| gtgctgaaga | cctcggctgg | gctgggactg | agtctggatg | ggaaaatc | atcggtgacg | 840 |
| ggagatgggc | ccttggtcat | aaaagagtg | tacaaaggtg | gtgcggctga | acaagctgga | 900 |
| ataatagaag | ctggagatga | aattcttgct | attaatggga | aacctctggt | tgggctcatg | 960 |
| cactttgatg | cctggaatat | tatgaagtct | gtcccagaag | gacctgtgca | gttattaatt | 1020 |
| agaaagcata | ggaattcttc | a | | | | 1041 |

<210> SEQ ID NO 3
<211> LENGTH: 36
<212> TYPE: DNA
<213> ORGANISM: Human

<400> SEQUENCE: 3
gttgttcata tgcttgacaa gctctgcagc gaggat    36

<210> SEQ ID NO 4
<211> LENGTH: 42
<212> TYPE: DNA
<213> ORGANISM: Human

<400> SEQUENCE: 4
gttgttctcg agtcatgaag aattcctatg ctttctaatt aa    42

<210> SEQ ID NO 5
<211> LENGTH: 350
<212> TYPE: PRT
<213> ORGANISM: Human

<400> SEQUENCE: 5

Ala Gly His Leu Asp Lys Leu Cys Ser Glu Asp Tyr Ser Ala Gly Pro
1               5                   10                  15

Ser Ala Val Leu Phe Lys Thr Glu Leu Glu Ile Thr Pro Arg Arg Ser
            20                  25                  30

Pro Gly Pro Pro Ala Gly Gly Val Ser Cys Pro Glu Lys Gly Gly Asn
        35                  40                  45

-continued

```
Arg Ala Cys Pro Gly Gly Ser Gly Pro Lys Thr Ser Ala Ala Glu Thr
     50                  55                  60
Pro Ser Ser Ala Ser Asp Thr Gly Glu Ala Ala Gln Asp Leu Pro Phe
 65                  70                  75                  80
Arg Arg Ser Trp Ser Val Asn Leu Asp Gln Leu Leu Val Ser Ala Gly
                 85                  90                  95
Asp Gln Gln Arg Leu Gln Ser Val Leu Ser Ser Val Gly Ser Lys Ser
            100                 105                 110
Thr Ile Leu Thr Leu Ile Gln Glu Ala Lys Ala Gln Ser Glu Asn Glu
            115                 120                 125
Glu Asp Val Cys Phe Ile Val Leu Asn Arg Lys Glu Gly Ser Gly Leu
            130                 135                 140
Gly Phe Ser Val Ala Gly Gly Thr Asp Val Glu Pro Lys Ser Ile Thr
145                 150                 155                 160
Val His Arg Val Phe Ser Gln Gly Ala Ala Ser Gln Glu Gly Thr Met
                165                 170                 175
Asn Arg Gly Asp Phe Leu Leu Ser Val Asn Gly Ala Ser Leu Ala Gly
            180                 185                 190
Leu Ala His Gly Asn Val Leu Lys Val Leu His Gln Ala Gln Leu His
            195                 200                 205
Lys Asp Ala Leu Val Val Ile Lys Lys Gly Met Asp Gln Pro Arg Pro
            210                 215                 220
Ser Ala Arg Gln Glu Pro Pro Thr Ala Asn Gly Lys Gly Leu Leu Ser
225                 230                 235                 240
Arg Lys Thr Ile Pro Leu Glu Pro Gly Ile Gly Arg Ser Val Ala Val
                245                 250                 255
His Asp Ala Leu Cys Val Glu Val Leu Lys Thr Ser Ala Gly Leu Gly
            260                 265                 270
Leu Ser Leu Asp Gly Gly Lys Ser Ser Val Thr Gly Asp Gly Pro Leu
            275                 280                 285
Val Ile Lys Arg Val Tyr Lys Gly Gly Ala Ala Glu Gln Ala Gly Ile
290                 295                 300
Ile Glu Ala Gly Asp Glu Ile Leu Ala Ile Asn Gly Lys Pro Leu Val
305                 310                 315                 320
Gly Leu Met His Phe Asp Ala Trp Asn Ile Met Lys Ser Val Pro Glu
                325                 330                 335
Gly Pro Val Gln Leu Leu Ile Arg Lys His Arg Asn Ser Ser
            340                 345                 350
```